United States Patent
Macinga et al.

(10) Patent No.: US 9,629,361 B2
(45) Date of Patent: *Apr. 25, 2017

(54) COMPOSITION AND METHOD FOR PRE-SURGICAL SKIN DISINFECTION

(75) Inventors: David R. Macinga, Stow, OH (US); Marcia Snyder, Stow, OH (US); James W. Arbogast, Bath, OH (US)

(73) Assignee: GOJO INDUSTRIES, INC., Akron, OH (US)

( * ) Notice: Subject to any disclaimer, the term of this patent is extended or adjusted under 35 U.S.C. 154(b) by 1294 days.

This patent is subject to a terminal disclaimer.

(21) Appl. No.: 11/647,952

(22) Filed: Dec. 29, 2006

(65) Prior Publication Data

US 2007/0184016 A1    Aug. 9, 2007

Related U.S. Application Data

(60) Provisional application No. 60/771,784, filed on Feb. 9, 2006.

(51) Int. Cl.
*A01N 33/12* (2006.01)
*A01N 37/36* (2006.01)

(52) U.S. Cl.
CPC ............ *A01N 33/12* (2013.01); *A01N 37/36* (2013.01)

(58) Field of Classification Search
None
See application file for complete search history.

(56) References Cited

U.S. PATENT DOCUMENTS

| | | | |
|---|---|---|---|
| 3,485,915 A | 12/1969 | Gerstein | 514/772.6 |
| 4,283,421 A | 8/1981 | Ray | 514/567 |
| 4,478,853 A | 10/1984 | Chaussee | 514/772 |
| 4,647,458 A | 3/1987 | Ueno et al. | 424/605 |
| 4,767,788 A | 8/1988 | Diana | 514/574 |
| 4,900,721 A | 2/1990 | Bansemir et al. | |
| 4,921,131 A | 5/1990 | Binderbauer | 222/52 |
| 4,956,170 A | 9/1990 | Lee | 514/772.1 |
| 5,000,867 A | 3/1991 | Heinhuis-Walther et al. | 510/384 |
| 5,043,357 A | 8/1991 | Hoffler | 514/553 |
| 5,084,096 A | 1/1992 | Stovicek | 106/18.21 |
| 5,145,663 A | 9/1992 | Simmons | 424/47 |
| 5,243,036 A | 9/1993 | Pablo Pivel Ranieri | 536/4.1 |
| 5,403,864 A | 4/1995 | Bruch | 514/721 |
| 5,441,723 A | 8/1995 | Simmons | 424/47 |
| 5,516,510 A | 5/1996 | Beilfuss | 424/65 |
| 5,629,006 A | 5/1997 | Hoang et al. | |
| 5,632,978 A | 5/1997 | Moore | 510/159 |
| 5,728,404 A | 3/1998 | von Rheinbaben et al. | |
| 5,770,199 A | 6/1998 | Eibl et al. | |
| 5,776,430 A | 7/1998 | Osborne | 424/43 |
| 5,885,562 A | 3/1999 | Lowry | 424/65 |
| 5,908,619 A | 6/1999 | Scholz | 424/78.02 |
| 5,939,085 A | 8/1999 | Jacobs | 424/401 |
| 5,942,218 A | 8/1999 | Kirschner et al. | |
| 5,944,912 A | 8/1999 | Jenkins | 134/40 |
| 5,951,993 A | 9/1999 | Scholz | 424/405 |
| 5,965,610 A | 10/1999 | Modak et al. | |
| 6,022,551 A | 2/2000 | Jampani | 424/405 |
| 6,025,314 A | 2/2000 | Nitsch | 510/221 |
| 6,034,133 A | 3/2000 | Hendley | 514/573 |
| 6,080,417 A | 6/2000 | Kramer | 424/405 |
| 6,090,395 A | 7/2000 | Asmus | 424/401 |
| 6,107,261 A | 8/2000 | Taylor | 510/131 |
| 6,110,908 A | 8/2000 | Guthery | 514/188 |
| 6,117,436 A | 9/2000 | Flemming | 424/401 |
| 6,136,771 A | 10/2000 | Taylor | 510/388 |
| 6,183,757 B1 * | 2/2001 | Beerse et al. | 424/401 |
| 6,183,768 B1 | 2/2001 | Harle | 424/423 |
| 6,204,230 B1 | 3/2001 | Taylor | 510/131 |
| 6,294,186 B1 | 9/2001 | Beerse et al. | |
| 6,319,958 B1 | 11/2001 | Johnson | 514/739 |
| 6,326,430 B1 | 12/2001 | Berte | 524/555 |
| 6,352,701 B1 * | 3/2002 | Scholz et al. | 424/405 |
| 6,423,329 B1 | 7/2002 | Sine et al. | 424/405 |
| 6,436,885 B2 | 8/2002 | Biedermann | 510/131 |
| 6,468,508 B1 | 10/2002 | Laughlin | 424/59 |
| 6,488,943 B1 | 12/2002 | Beerse | 424/401 |
| 6,517,855 B2 | 2/2003 | Prusiner | 424/408 |
| 6,534,069 B1 | 3/2003 | Asmus | 424/401 |

(Continued)

FOREIGN PATENT DOCUMENTS

| | | |
|---|---|---|
| CA | 2222498 | 10/1997 |
| DE | 4221743 | 1/1994 |

(Continued)

OTHER PUBLICATIONS

Kampf, Günter et al., "Epidemiologic Background of Hand Hygiene and Evaluation of the Most Important Agents for Scrubs and Rubs," Clinical Microbiology Reviews, vol. 17, Oct. 2004, p. 863-893.
European Search Report for European Appl. No. EP 07 25 0492 dated Jul. 10, 2007, 11 pages.
Office Action dated Apr. 15, 2008 for copending U.S. Appl. No. 11/499,227, 10 pages.
Office Action dated Dec. 1, 2008 for copending U.S. Appl. No. 11/499,227, 14 pages.
Final Office Action dated May 28, 2009 for copending U.S. Appl. No. 11/499,227, 18 pages.
Advisory Action dated Aug. 20, 2009 for copending U.S. Appl. No. 11/499,227, 4 pages.
Office Action dated Aug. 21, 2012 for JP Appl. No. 2008-554302 issued by Japanese Patent Office; English translation attached; 9 pages.
Can. J. Biochem., 1981, vol. 59, No. 10, pp. 799-801.
Journal of the Japanese Assoication for Infectious Diseases, 1981, vol. 55, No. 5, pp. 367-372; English abstract only attached.
J. Virol. Methods, 1982, vol. 5, No. 5, pp. 285-291.

(Continued)

*Primary Examiner* — Nissa Westerberg
(74) *Attorney, Agent, or Firm* — Renner Kenner Greive Bobak Taylor and Weber

(57) ABSTRACT

This invention provides a pre-surgical disinfecting composition that includes at least about 50 percent by weight of a $C_{1-6}$ alcohol, based upon the total weight of the disinfecting composition, an acid, and a cationic oligomer or polymer. A method for pre-surgical skin disinfection with rapid antiseptic efficacy without the use of secondary antimicrobial compounds is also described.

8 Claims, No Drawings

(56) References Cited

U.S. PATENT DOCUMENTS

| | | | |
|---|---|---|---|
| 6,569,261 B1 | 5/2003 | Aubay | 134/39 |
| 6,582,711 B1 | 6/2003 | Asmus | 424/405 |
| 6,610,314 B2 | 8/2003 | Koenig | 424/402 |
| 6,613,755 B2 | 9/2003 | Peterson | 514/63 |
| 6,623,744 B2 | 9/2003 | Asmus | 424/401 |
| 6,645,507 B2 | 11/2003 | Bettle | 424/401 |
| 6,685,952 B1 | 2/2004 | Ma | 424/401 |
| 6,719,988 B2 | 4/2004 | Prusiner | 424/405 |
| 6,720,355 B2 | 4/2004 | Prusiner | 514/557 |
| 6,723,689 B1 | 4/2004 | Hoang et al. | 510/130 |
| 6,805,874 B1 | 10/2004 | Lutz | 424/401 |
| 6,838,078 B2 | 1/2005 | Wang et al. | 424/78.02 |
| 6,846,846 B2 | 1/2005 | Modak et al. | |
| 6,894,012 B2 | 5/2005 | Sebillotte-Arnaud | 510/136 |
| 7,670,615 B2 | 3/2010 | Veeger et al. | |
| 7,803,390 B2 | 9/2010 | Asmus et al. | |
| 8,119,115 B2 | 2/2012 | Snyder et al. | |
| 2002/0161046 A1 | 10/2002 | Konowalchuk | 514/557 |
| 2002/0165278 A1 | 11/2002 | Konowalchuk | 514/557 |
| 2002/0165279 A1 | 11/2002 | Konowalchuk | 514/557 |
| 2003/0008791 A1 | 1/2003 | Chiang | |
| 2003/0118619 A1 | 6/2003 | Suares | 424/401 |
| 2003/0215418 A1 | 11/2003 | Asmus | 424/78.35 |
| 2004/0001797 A1 | 1/2004 | Saud | 424/70.16 |
| 2004/0063591 A1 | 4/2004 | Borazjani et al. | |
| 2004/0127559 A1 | 7/2004 | Prusiner | 514/517 |
| 2004/0247685 A1* | 12/2004 | Modak et al. | 424/488 |
| 2005/0025833 A1 | 2/2005 | Aschkenasy | 424/484 |
| 2005/0058673 A1 | 3/2005 | Scholz | 424/401 |
| 2005/0089539 A1 | 4/2005 | Scholz | 424/401 |
| 2005/0119221 A1 | 6/2005 | Xia et al. | |
| 2005/0129644 A1 | 6/2005 | Sabbagh et al. | |
| 2005/0182021 A1 | 8/2005 | Nichols et al. | |
| 2005/0228351 A1 | 10/2005 | Bret et al. | |
| 2005/0238602 A1 | 10/2005 | Modak | 424/70.11 |
| 2006/0008494 A1 | 1/2006 | Prusiner | 424/405 |
| 2006/0051384 A1 | 3/2006 | Scholz et al. | 424/405 |
| 2006/0052452 A1 | 3/2006 | Scholz | 514/557 |
| 2006/0074108 A1 | 4/2006 | Gupta | |
| 2006/0182690 A1 | 8/2006 | Veeger et al. | |
| 2006/0204466 A1 | 9/2006 | Littau et al. | 424/70.13 |
| 2006/0204467 A1 | 9/2006 | Littau et al. | 424/70.13 |
| 2006/0205619 A1 | 9/2006 | Mayhall et al. | 510/130 |
| 2006/0281663 A1 | 12/2006 | Asmus et al. | |
| 2007/0065383 A1 | 3/2007 | Fernandez de Castro et al. | |
| 2007/0148101 A1 | 6/2007 | Snyder et al. | 424/47 |
| 2007/0179207 A1 | 8/2007 | Fernandez de Castro et al. | |
| 2007/0184016 A1 | 8/2007 | Macinga et al. | |
| 2007/0185216 A1 | 8/2007 | Snyder et al. | |
| 2007/0258911 A1 | 11/2007 | Fernandez de Castro et al. | |
| 2009/0018213 A1 | 1/2009 | Snyder et al. | |
| 2009/0098067 A1 | 4/2009 | Seidling et al. | |
| 2010/0022660 A1 | 1/2010 | Wegner et al. | |
| 2010/0069505 A1 | 3/2010 | Veeger et al. | |
| 2012/0134952 A1 | 5/2012 | Snyder et al. | |

FOREIGN PATENT DOCUMENTS

| | | |
|---|---|---|
| EP | 0222579 | 5/1987 |
| EP | 491643 | 6/1992 |
| EP | 604848 | 7/1994 |
| EP | 707794 | 4/1996 |
| EP | 963158 | 12/1999 |
| EP | 1120040 A2 | 8/2001 |
| EP | 1125498 | 8/2001 |
| GB | 1126953 | 9/1968 |
| GB | 2087724 | 6/1982 |
| GB | 2187097 | 9/1987 |
| GB | 2391810 | 2/2004 |
| JP | 504175/95 A | 5/1995 |
| JP | 8198709 A | 8/1996 |
| JP | 2004 137199 A | 5/2004 |
| JP | 2004 143074 A | 5/2004 |
| WO | 94/27440 A1 | 12/1994 |
| WO | 98/30095 | 7/1998 |
| WO | 01/28340 | 4/2001 |
| WO | WO 01/28339 | 4/2001 |
| WO | WO 03/034994 | 5/2003 |
| WO | WO 03/052452 | 6/2003 |
| WO | 2004/062589 A2 | 7/2004 |
| WO | 2004/101726 | 11/2004 |
| WO | 2005/030917 A1 | 4/2005 |
| WO | 2005/037242 A1 | 4/2005 |
| WO | WO 2005/067878 | 7/2005 |
| WO | 2005/092273 A2 | 10/2005 |
| WO | 2005/105070 | 11/2005 |
| WO | WO 2005/110090 A1 | 11/2005 |
| WO | WO 2006/02349 | 3/2006 |
| WO | WO 2006/029255 | 3/2006 |
| WO | 2006/062835 | 6/2006 |
| WO | 2006/062845 | 6/2006 |
| WO | 2006/062846 | 6/2006 |
| WO | 2006/062847 | 6/2006 |
| WO | 2006/062857 | 6/2006 |
| WO | 2006/062897 | 6/2006 |
| WO | 2006/066888 A2 | 6/2006 |
| WO | 2006/094387 A1 | 9/2006 |
| WO | WO 2006/099358 | 9/2006 |
| WO | WO2007/016067 | 2/2007 |
| WO | WO 2007/044032 A2 | 2/2007 |
| WO | WO 2007/024973 | 3/2007 |
| WO | 2007/095008 A2 | 8/2007 |
| WO | WO/2008/049454 | 5/2008 |

OTHER PUBLICATIONS

Antimicrob. Agents Chemother., 1984, vol. 26, No. 6, pp. 928-929.

Office Action dated Jun. 17, 2010 for copending U.S. Appl. No. 11/499,227; 23 pages.

Sickbert-Bennett, Emily E. et al., "The effects of test variables on the efficacy of hand hygiene agents," Am J Infect Control, 2004, vol. 32, p. 69-83.

Sofer, Gale et al., Part 6, Inactivation Methods Grouped by Virus, BioPharm International, 2003, Supplement S-37-S-42.

Sattar, Syed et al., "Activity of an Alcohol-Based Hand Gel Against Human Adeno-, Rhino-, and Rotaviruses Using the Fingerpad Method," Infection Control and Hospital Epidemiology, 2000, vol. 21, p. 516-519.

Kramer, A. et al., "Virucidal activity of a new hand disinfectant with reduced ethanol content: comparison with other alcohol-based formulations," Journal of Hospital Infection, Jan 2006, vol. 62, p. 98-106.

Piret, J. et al., "Sodium Lauryl Sulfate, a Microbicide Effective Against Enveloped and Nonenveloped Viruses," Current Drug Targets, 2002, vol. 3, p. 17-30.

Dick, Elliot C. et al., "Interruption of Transmission of Rhinovirus Colds Among Human Volunteers Using Virucidal Paper Handkerchiefs," Feb. 1986, J. of Infectious Diseases, vol. 158, No. 2, p. 352-356.

Turner, Ronald B. et al., "Virucidal Hand Treatments for Prevention of Rhinovirus Infection," Sep. 13, 2005, J. of Antimicrobial Chemotherapy; p. 1-3.

Turner, Ronald B. et al., "Efficacy of Organic Acids in Hand Cleaners for Prevention of Rhinovirus Infections," Jul. 2004, Antimicrobial Agents and Chemotherapy, vol. 48, No. 7, p. 2595-2598.

Turner, Ronald B., "New Considerations in the Treatment and Prevention of Rhinovirus Infections," Jan. 2005, Pediatric Annals, 34:1, p. 53-60.

Turner, Ronald B., "The Treatment of Rhinovirus Infections: Progress and Potential," 2001, Antiviral Research, 49 (2001), pp. 1-14.

Standardization News; "Anti-Microbial Characteristics of Copper," vol. 14; No. 19; Oct. 2006, p. 2-6.

Gruber, J.V., "Polysaccharide-based Polymers in Cosmetics", Chapter 8, Cosmetic Science and Technology Series, vol. 22, 1999, Principles of polymer science and technology in cosmetics and personal care, edited by E. Desmond and James V. Gruber, 65 pages in pdf (no page numbers).

Gehrke et al., Journal of Hospital Infection, 2004, 56 pp. 49-55.

Goodman & Gilman's "The Pharmacological Basis of Therapeutics", (9th ed 1996), p. 43-62.

(56) References Cited

OTHER PUBLICATIONS

Liu, Pengbo, "Comparative Efficacy of Alcohol-based Hand Sanitizers and Antibacterial Foam Handwash against Noroviruses Using the Fingerpad Method," Research report presented at the 94th Annual AIFP Meeting, Jul. 8, 2007.

* cited by examiner

COMPOSITION AND METHOD FOR PRE-SURGICAL SKIN DISINFECTION

RELATED APPLICATIONS

This application claims priority from U.S. Provisional Patent Application Ser. No. 60/771,784, filed on Feb. 9, 2006, which is hereby incorporated by reference.

TECHNICAL FIELD

The present invention relates to a composition and method for pre-surgical skin disinfection with rapid antiseptic efficacy without the use of secondary antimicrobial compounds.

BACKGROUND OF THE INVENTION

Standard surgical procedures require disinfection of skin surfaces of the surgeon, the operating staff, and patient at the surgical site prior to surgery. Effective pre-operative cleansing of skin is critical to reducing the risk of infection to the patient. Surgical scrub and pre-operative skin preparations are therefore important to control the risk of infection.

Microorganisms on the skin can be transient or resident. Transient microorganisms are introduced onto the skin via the environment and lie on the surface of the skin, whereas resident microorganisms are evolved to survive and grow on the skin and are found at the surface as well as at deeper sites in the skin.

Surgical hand antisepsis is an antiseptic handwash or antiseptic hand rub performed preoperatively by surgical personnel to eliminate transient and reduce resident hand flora. This may also be referred to as disinfection. Patient skin antisepsis is also required to disinfect the site of the surgery.

Effective antiseptic compositions can be produced by combining a surfactant or detergent with an antimicrobial agent. However, many such compositions are harsh or unsuitable for contact with human skin, and can cause discomfort and irritation to the skin. The development of formulations containing antimicrobial agents and detergents that provide acceptable antiseptic properties as well as avoid skin irritation has proven difficult, since the effectiveness of the antimicrobial agent is often reduced by the additional ingredients used.

United States Food and Drug Administration (FDA) developed performance standards for new and novel antiseptic compositions. These performance standards require a surgical hand scrub to be broad spectrum, fast acting, and persistent. The term broad spectrum is defined in this instance as having antimicrobial activity against a variety of gram positive and gram negative bacteria, and yeasts. The FDA also set forth testing procedures by which new antiseptics are tested alongside previously approved products. Requirements for patient preoperative skin preparation are outlined in the FDA Tentative Final Monograph for Healthcare Antiseptic Drug Products (TFM) (Federal Register 59 [116], Jun. 17, 1994: pp. 31402-31452).

Requirements for in vitro and in vivo testing of surgical hand scrubs are outlined in the FDA Tentative Final Monograph for Healthcare Antiseptic Drug Products (TFM) (Federal Register 59 [116], Jun. 17, 1994: pp. 31445-31448). The in vivo test procedure described beginning on page 31445 will hereinafter be referred to as the FDA TFM surgical hand scrub test.

The antimicrobial efficacy of Surgical Scrubs can also be tested by any appropriate recognized test to demonstrate adequate disinfection of resident skin flora. Examples of such tests are ASTM E 1115-02, "Standard Test Method for Evaluation of Surgical Hand Scrub Formulations" (ASTM International) and EN 12791:2005, "Chemical disinfectants and antiseptics, Surgical hand disinfection, Test method and requirement (phase 2, step 2)," (CEN-Comitée Européen de Normalisation, Brussels, Belgium). ASTM E 1173-01 provides "Standard Test Method for Evaluation of Preoperative, Precatheterization, or Preinjection Skin Preparations."

The product to be tested according to the FDA TFM surgical hand scrub test is used eleven times over a period of five days, and the reduction of resident skin flora is measured after the first wash on days 1, 2, and 5. Measurements are also done 3 and 6 hours after these washes, to measure persistence. The FDA TFM surgical hand scrub test requires that formulations reduce the number of bacteria 1 $\log_{10}$ on each hand within 1 minute of product application and that the bacterial cell count on each hand does not subsequently exceed baseline within 6 hours on day 1; the formulation must produce a 2 $\log_{10}$ reduction in microbial flora on each hand within 1 minute of product application by the end of the second day of enumeration and a 3 $\log_{10}$ reduction of microbial flora on each hand within 1 minute of product use by the end of the fifth day when compared with the established baseline.

Numerous attempts have been made to develop formulations that provide effective antiseptic or disinfectant properties and that meet the requirements of the glove juice test. However, the efficacy of antiseptic or disinfectant compositions is greatly influenced by a number of variables, including concentration of organisms, duration of exposure, concentration of the antiseptic and the type of surfactants used in the formulation.

Formulations containing the antimicrobial agent chlorhexidine have been used as antibacterial skin cleaners in surgical scrubs. For example, Billany et al., U.S. Pat. No. 3,960,745, discloses a chlorhexidine cleansing composition formulated with a polyoxyethylene-polyoxypropylene non ionic surfactant.

Other formulations have used bisbiguanide as an antimicrobial agent as disclosed in U.S. Pat. No. 4,456,543 to Ownes. The '543 patent discloses an antibacterial cleansing formulation containing bisbiguanide and one or more non-ionic polyoxyalkylene surfactants.

Dewar et al., U.S. Pat. No. 4,157,977 discloses surfactant-germicide compositions containing an antimicrobial active phenolic derivative in combination with hydroxyacetic acid and a surfactant.

Casey et al., U.S. Pat. No. 4,252,665 and Langguth et al., U.S. Pat. No. 4,257,907 disclose a disinfectant cleaning composition containing ortho-benyzl-para-chlorophenol, anionic surfactants and sulfobetaine surfactants.

Meldovanyl et al., United Kingdom Application 2 203 339, discloses an aqueous microbicidal formulation containing (A) a microbicidal active substance such as benzalkonium chloride, (B) a dispersing active substance such as certain carboxylic acids, and (C) a solubilizing agent such as propylene glycol.

Formulations containing the antimicrobial agent parachlorometaxylenol (PCMX) have been disclosed in a number of patents. U.S. Pat. No. 4,632,772 to Garabedian et al. discloses an antimicrobial composition containing the active antimicrobial agent PCMX and an ionic surfactant, alkyl aryl ethoxylated sulfonate. Melvin, U.S. Pat. No. 3,326,808 discloses an antiseptic surfactant composition containing PCMX and an anionic surfactant, the sodium salt of 2-sulfomethyl myristate. U.S. Pat. No. 6,413,921 teaches a composition that can be used as a surgical scrub formulation or pre-surgical skin disinfecting formulation. The pre-operative antimicrobial skin composition comprises parachlorometaxylenol (PCMX) as the antimicrobial agent and an anionic surfactant composition comprising a surfactant having a hydrophobic portion consisting of a linear alkyl and a hydrophilic portion having ethoxylation termination with a sulfonate anionic group; and a sarcosine surfactant.

Because of the rapid bactericidal activity of lower alcohols, numerous inventions have centered around alcohol-containing surgical scrub technologies. White, European Patent Application 0 223 681, discloses an alcohol-based antimicrobial composition that includes a viscosifying agent such as hydroxypropyl cellulose.

U.S. Pat. No. 6,110,908 to Guthery teaches an antiseptic composition claiming broad spectrum, fast acting and persistent effect, that includes 70% antibacterial alcohol, an antimicrobial lipid such as free fatty acids and/or fatty acid esters, and zinc pyrithione or zinc omadine. However, free fatty acids can be skin irritants. Also, compositions containing zinc pyrithione or zinc omadine are generally solid suspensions, and separation can occur over time, shortening shelf-life of the product.

U.S. Pat. No. 6,090,395 teaches a viscous pre-surgical scrub containing a lower alcohol and water in a weight ratio of about 35:65 to about 100:0, which is thickened to a viscosity of at least 4,000 centipoise, by using an emulsifier system. A secondary antimicrobial component such as chlorhexidine gluconate (CHG) may be added to achieve the efficacy required for surgical scrubs. However, it has been found that irritation due to CHG sensitivity can occur.

U.S. Pat. No. 6,723,689 teaches an antimicrobial composition that includes alcohol in an amount from about 60 to about 95 weight percent, a preservative, a cationic cellulose polymer thickening agent, a moisturizer and/or a cationic emulsifier, and water. The antimicrobial composition was tested according to the FDA glove juice test, and exhibited a 3.03 log kill on day 3 of the test (3.47 log kill when 4 percent by weight CHG was added). The compositions reported to pass the FDA requirements for surgical scrubs contain CHG. As stated above, CHG sensitivity can result in irritation to the skin. The '689 patent includes comparative test data showing that formulations according to the '908 patent and the '395 patent did not meet the 3 log kill requirement as of day 3.

U.S. Published application No. 2004/0247685 A1 teaches a hydroalcoholic antimicrobial composition that includes octoxyglycerin (Sensiva®) and at least one other antimicrobial agent, such as biguanides or phenols. U.S. Published application No. 2005/0238602 A1 teaches a hydroalcohol gel surgical hand wash comprising: (i) two or more organic salts of zinc; (ii) farnesol; (iii) panthenol; and (iv) a quaternary ammonium compound and a biguanide. In order to maintain antimicrobial efficacy, these components are used in conjunction with various combinations of chlorhexidine gluconate, benzalkonium chloride, incroquat and Sensiva.® There is no suggestion that the compositions of the '602 or '685 published applications have adequate antimicrobial efficacy without these additional antimicrobial agents.

U.S. Pat. No. 6,319,958 describes attempts to increase the efficacy of antimicrobial agents by using sesqueterpenoids. However, studies suggest that sesqueterpenoids can cause irritation to human skin.

Therefore, each of the current pre-surgical disinfecting products has one or more short-comings. These short-comings include irritation to the skin, stickiness, a greasy feel, and inadequate efficacy. A need continues to exist for topical compositions that have rapid efficacy against both transient and resident microorganisms on the skin, very low toxicity, and good aesthetics. More specifically, it would be desirable to have a surgical scrub and pre-operative skin preparation without the above shortcomings that meets the requirements for antiseptics as outlined in the FDA Tentative Final Monograph for Healthcare Antiseptic Drug Products (TFM). Particularly, it would be desirable to have a surgical hand scrub that meets the requirements of the FDA TFM surgical hand scrub test.

SUMMARY OF THE INVENTION

This invention provides a pre-surgical disinfecting composition comprising at least about 50 percent by weight of a $C_{1-6}$ alcohol, based upon the total weight of the disinfecting composition, an acid selected from mineral acids, organic acids, or mixtures thereof; and a cationic oligomer or polymer, wherein said composition provides a log kill of greater than about 3 in less than about 3 minutes against resident and transient skin flora.

The invention also provides a method for pre-surgical hand disinfection, the method comprising contacting the skin with an effective amount of a disinfecting composition comprising at least about 50 percent by weight of a $C_{1-6}$ alcohol, based upon the total weight of the disinfecting composition; an acid; and a cationic oligomer or polymer.

The invention further provides a method for pre-operative skin disinfection, the method comprising contacting the skin with an effective amount of a disinfecting composition comprising at least about 50 percent by weight of a $C_{1-6}$ alcohol, based upon the total weight of the disinfecting composition; an acid; and a cationic oligomer or polymer.

DETAILED DESCRIPTION OF ILLUSTRATIVE EMBODIMENTS

The present invention provides a pre-surgical disinfecting composition with rapid bactericidal efficacy without the need for secondary antimicrobial compounds or preservatives. In one or more embodiments, the disinfecting composition meets or exceeds the FDA TFM surgical hand scrub test by demonstrating greater than (>) 3 log kill of redicent and transient skin flora after 5 days of product use.

In another embodiment, the disinfecting composition exceeds the FDA TFM surgical hand scrub test by demonstrating greater than (>) 3 log kill after a single product use. More specifically, in one or more embodiments, the composition provides a log kill of greater than about 3 in less than about 3 minutes against resident and transient skin flora. In one embodiment, the composition provides a log kill of greater than about 3 in less than about 2 minutes against resident and transient skin flora, and in another embodiment, the composition provides a log kill of greater than about 3 in less than about 1 minute against resident and transient skin flora.

The disinfecting composition comprises a $C_{1-6}$ alcohol, an acid, and a cationic oligomer or polymer. In one embodiment, the alcohol is a lower alkanol, i.e. an alcohol containing 1 to 6 carbon atoms. Typically, these alcohols have antimicrobial properties. Examples of lower alkanols include, but are not limited to, methanol, ethanol, propanol, butanol, pentanol, hexanol, and isomers and mixtures thereof. In one embodiment, the alcohol comprises ethanol, propanol, or butanol, or isomers or mixtures thereof. In another embodiment, the alcohol comprises ethanol.

Generally, the disinfecting composition comprises at least about 50 percent by weight alcohol, based upon the total weight of the disinfecting composition. In one embodiment, the disinfecting composition comprises at least about 60 weight percent alcohol, in another embodiment, the disinfecting composition comprises at least about 65 weight percent alcohol, in yet another embodiment, the disinfecting composition comprises at least about 70 weight percent alcohol, and in still yet another embodiment, the disinfecting composition comprises at least about 78 weight percent alcohol, based upon the total weight of disinfecting composition. More or less alcohol may be required in certain instances, depending particularly on other ingredients and/or the amounts thereof employed in the composition. In certain embodiments, the disinfecting composition comprises from about 50 weight percent to about 98 weight percent alcohol, in other embodiments, the disinfecting composition comprises from about 60 weight percent to about 95 weight percent of alcohol, in yet other embodiments, the disinfecting composition comprises from about 65 weight percent to about 90 weight percent of alcohol, and in still other embodiments, the disinfecting composition comprises from about 70 weight percent to about 85 weight percent of alcohol, based upon the total weight of the disinfecting composition.

In certain embodiments, the acid includes a mineral acid, organic acid, or mixtures thereof. Strong or weak acids may be used. Examples of mineral acids include inorganic acids such as hydrochloric acid, nitric acid, sulfuric acid, phosphonic acid, phosphoric acid, and boric acid. Organic acids include adipic acid, benzene 1,3,5 tricarboxylic acid, chlorosuccinic acid, choline chloride, cis-aconitic acid, citramalic acid, citric acid, cyclobutane 1,1,3,3 tetracarboxylic acid, cyclohexane 1,2,4,5 tetracarboxylic acid, cyclopentane 1,2,3,4 tetracarboxylic acid, diglycolic acid, fumaric acid, glutamic acid, glutaric acid, glyoxylic acid, isocitric acid, ketomalonic acid, lactic acid, maleic acid, malic acid, malonic acid, nitrilotriacetic acid, oxalacetic acid, oxalic acid, phytic acid, p-toluenesulfonic acid, salicylic acid, succinic acid, tartaric acid, tartronic acid, tetrahydrofuran 2,3,4,5 tetracarboxylic acid, tricarballylic acid, versene acids, 3-hydroxyglutaric acid, 2-hydroxypropane 1,3 dicarboxylic acid, glyceric acid, furan 2,5 dicarboxylic acid, 3,4-dihydroxyfuran-2,5 dicarboxylic acid, 3,4-dihydroxytetrahydrofuran-2,5-dicarboxylic acid, 2-oxo-glutaric acid, diglyceric acid, and 2,5 furandicarboxylic acid.

In one embodiment, the organic acid includes an alpha-hydroxy carboxylic acid, and in one embodiment, the alpha-hydroxy acid includes two or more carboxylic acid groups. Examples of alpha-hydroxy acids having two or more carboxylic acid groups include tartaric acid, malic acid, citric acid, and isocitric acid. In one embodiment, the organic acid includes citric acid. In one or more embodiments, the organic acid includes citric acid, lactic acid, malic acid, tartaric acid, salicylic acid, oxalic acid, or mixtures thereof. In one embodiment, the organic acid includes citric acid.

In one embodiment, the acid is added in an amount of from about 0.012 to about 1 weight percent, based upon the total weight of the disinfecting composition. In another embodiment, the amount of acid is from about 0.015 to about 0.5 weight percent, and in yet another embodiment, from about 0.039 to about 0.3 weight percent, based upon the total weight of the disinfecting composition. It will be understood that greater levels of acid can be used, if desired, and are expected to perform equally as well.

In one embodiment, the acid is added to the disinfecting composition as a solution or emulsion. In other words, the acid may be premixed with a carrier to form an acid solution or emulsion, with the proviso that the carrier does not deleteriously affect the disinfecting properties of the composition. More specifically, a carrier deleteriously affects the disinfecting properties of the composition when it decreases the log kill by more than a de minimus amount. By de minimus is meant a decrease of less than about 0.5 log kill.

Examples of carriers include water, alcohol, or blends of water and another carrier such as glycols, ketones, linear and/or cyclic hydrocarbons, triglycerides, carbonates, silicones, alkenes, esters such as acetates, benzoates, fatty esters, glyceryl esters, ethers, amides, polyethylene glycols, PEG/PPG copolymers, inorganic salt solutions such as saline, and mixtures thereof. It will be understood that, when the acid is premixed to form an acid solution or emulsion, the amount of solution or emulsion that is added to the disinfecting composition is selected so that the amount of acid falls within the ranges set forth hereinabove.

It has been found that, in certain embodiments, a cationic oligomer or polymer enhances the disinfectant efficacy of alcoholic solutions against transient and resident flora on skin. Cationic oligomers and polymers include molecules having three or more repeat units, and are therefore completely distinct from cationic materials that occur in their primary form as single molecules or dimers.

Cationic oligomer or polymers include, but are not limited to, cationic polysaccharides, cationic copolymers of saccharides and synthetic cationic monomers, and synthetic cationic oligomer or polymers. Synthetic cationic oligomers or polymers include cationic polyalkylene imines, cationic ethoxy polyalkylene imines, cationic poly[N-[3-(dialkylammonio)alkyl]N[3-(alkyleneoxyalkylene dialkylammonio) alkyl]urea dichloride], vinyl caprolactam/VP/dialkylaminoalkyl alkylate copolymers, and polyquaternium polymers.

Examples of cationic oligomers or polymers include chitosan, copolymers of isophorone diisocyanate and PEG-15 cocamine, vinyl caprolactam/VP/dimethylaminoethyl methacrylate copolymer, polyquaternium-4/hydroxypropyl starch copolymer, butylmethacrylate-(2-dimethylaminoethyl)methacrylate-methylmethacrylate-copolymer, guar hydroxypropyl trimonium chloride and dilinoleyl amidopropyl dimethylammonium chloride hydroxypropyl copolymer. Examples of polyquaterniums include those listed in Table 1, below, including the INCI name and technical name.

TABLE 1

| INCI Name Polyquaternium-X | Technical Name |
|---|---|
| -2 | Bis(2-chloroethyl)ether, polym. w. N,N'-bis[3-dimethylamino)propyl]urea |
| -4 | Hydroxyethylcellulose Dimethyldiallylammoinum Chloride Copolymer |

TABLE 1-continued

| INCI Name Polyquaternium-X | Technical Name |
|---|---|
| -5 | Copolymer of acrylamide and beta-methacrylyloxyethyl trimethyl ammonium methosulfate |
| -6 | Polydimethyldiallyl Ammonium Chloride |
| -7 | Dimethyldiallyl Ammonium Chloride & Acrylamide Copolymer |
| -9 | Polydimethyaminoethyl methacrylate quaternized with Methyl Bromide |
| -10 | Hydroxyethylcellulose reacted with trimethyl ammonium substituted epoxide |
| -11 | PVP N,N-Dimethyl Aminoethyl Methacrylic Acid Copolymer Diethyl Sulfate Soln |
| -14 | Ethanaminium, N,N,N-Trimethyl-2-[(2-methyl-1-oxo-2-propenyl)oxy]-, Methyl Sulfate Homopolymer |
| -15 | Acrylamide-Dimethylaminoethyl Methacrylate Methyl Chloride Copolymer |
| -16 | 3-Methyl-1-Vinylimidazolium Chloride-1-Vinyl-2-Pyrrolidinone Chloride |
| -17 | Quat salt made from Adipic acid & diethylaminopropylamine & dichloroether |
| -18 | Quat salt prepared by the reaction of adipic acid and dimethylaminopropylamine, reacted with dichloroethyl ether |
| -19 | Quat ammonium salt prepared by the reaction of polyvinyl alcohol with 2,3-epoxypropylamine |
| -20 | Quat ammonium salt prepared by the reaction of polyvinyl octadecyl ether with 2,3-epoxypropylamine |
| -22 | Acrylic Acid-Diallyldimethylammonium Chloride (DADMAC) Polymer |
| -24 | Polyquat ammonium salt of hydroxyethyl cellulose reacted with lauryl dimethyl ammonium substituted epoxide |
| -27 | Block Copolymer of Polyquaternium-2 and 17 |
| -28 | Vinylpyrrolidone/Methacrylamidopropyltrimethylammonium Chloride Copolymer |
| -29 | Propoxylated Chitosan quaternized with epichlorhydrin |
| -30 | Ethanaminium, N-Carboxymethyl)-N,N-Dimethyl-2-((2-Methyl-1-Oxo-2-Propenyl)Oxy)-, Inner Salt, Polymer with Methyl 2-Methyl-2-Propenoate |
| -31 | 2-propane nitrile reaction product w/ N,N-dimethylpropanediamine, Sulfate |
| -32 | Acrylamide-Dimethylaminoethyl Methacrylate Methyl Chloride (DMAEMA) Copolymer |
| -37 | Trimethylaminoethyl Methacrylate Chloride Polymer |
| -39 | Acrylic Acid (AA), Polymer w/ Acrylamide & Diallyldimethylammonium Chloride(DADMAC) |
| -42 | Polyoxyethylene (dimethyliminio)ethylene-(dimethyliminio)ethylene dichloride |
| -43 | Copolymer of Acrylamide, acrylamidopropyltrimonium chloride, amidopropylacrylamide & DMAPA Monomers |
| -44 | Polyquat ammonium salt of vinylpyrrilidone & quaternized imidazoline monomers |
| -46 | Quat ammonium salt of vinylcaprolactum, vinylpyrrolidone &methylvinylimidazolium |
| -47 | Quat ammonium chloride-acrylic acid, methyl acrylate & methacrylamidopropyltrimonium Chloride |
| -48 | Copolymer of methacryolyl ethyl betaine, 2-hydroxyethylmethacrylate & methacryloylethyltrimethylammonium chloride |
| -51 | 3,5,8-Triox-4-Phosphaundec-10-en-1-aminium, 4-Hydroxy-N,N,N,10-Tetramethyl-9-Oxo, Inner Salt, 4-Oxide, Polymer with Butyl 2-Methyl-2-Propenoate |
| -53 | Acrylic Acid (AA)/Acrylamide/Methacrylamidopropyltrimonium Chloride (MAPTAC) Copolymer |
| -54 | Polymeric quaternary ammonium salt prepared by the reaction of aspartic acid and C6–18 alkylamine with dimethylaminopropylamine and sodium chloroacetate |
| -55 | 1-Dodecanaminium, N,N-Dimethyl-N-[3-[(2-Methyl-1-Oxo-2-Propenyl)AminoPropyl]-, Chloride, Polymer with N-[3-(Dimethylamino)Propyl]-2-Methyl-2-Propenamide and 1-Ethenyl-2-Pyrrolidinone |
| -56 | Polymeric quaternary ammonium salt prepared by the reaction of aspartic acid and C6–18 alkylamine with dimethylaminopropylamine and sodium chloroacetate. |
| -57 | Polymeric quaternary ammonium salt consisting of Castor Isostearate Succinate (q.v.) and Ricinoleamidopropyltrimonium Chloride (q.v.) monomers |
| -58 | 2-Propenoic Acid, Methyl Ester, Polymer with 2,2-Bis[(2-Propenyloxy)Methyl]-1-Butanol and Diethenylbenzene, Reaction Products with N,N-Dimethyl-1,3-Propanediamine, Chloromethane-Quaternized |
| -59 | Polyquaternium polyester |

TABLE 1-continued

| INCI Name Polyquaternium-X | Technical Name |
| --- | --- |
| -60 | 9-Octadecenoic Acid, 12-Hydroxy-, [(2-Hydroxyethyl)Imino]Di-2,1-Ethanediyl Ester, Polymer with 5-Isocyanato-1-(Isocyanatomethyl)-1,3,3-Trimethylcyclohexane, Compd. with Diethyl Sulfate |
| -62 | Polymeric quaternary ammonium salt prepared by the reaction of butyl methacrylate, polyethylene glycol methyl ether methacrylate, ethylene glycol dimethacrylate and 2-methacryloyethyl trimonium chloride with 2,2'-azobis(2-methyl propionamidine) dihydrochloride |
| -63 | Copolymer of acrylamide, acrylic acid and ethyltrimonium chloride acrylate |
| -65 | Polymeric quaternary ammonium salt consisting of 2-methacryloyloxyethylphosphorylcholine, butyl methacrylate and sodium methacrylate monomers |
| -68 | Quaternized copolymers of vinylpyrrolidone (VP), methacrylamide(MAM) vinylimidazole(VI) & quaternized vinylimidazole (QVI) |
| -69 | Polymeric quaternary ammonium salt containing vinyl caprolactam, vinylpyrrolidone, dimethylaminopropyl methacrylamide (DMAPA), and methoacryloylaminopropyl lauryldimonium chloride |
| -70 | |
| -71 | |
| -72 | |
| -73 | |
| -74 | |
| -75 | |

In one or more embodiments, the polyquaternium polymer includes polyquaternium-2, polyquaternium-4, polyquaternium-5, polyquaternium-6, polyquaternium-7, polyquaternium-10, polyquaternium-11, polyquaternium-16, polyquaternium-22, polyquaternium-24, polyquaternium-28, polyquaternium-32, polyquaternium-37, polyquaternium-39, polyquaternium-42, polyquaternium-43, polyquaternium-44, polyquaternium-46, polyquaternium-47, polyquaternium-51, polyquaternium-53, polyquaternium-55, polyquaternium-57, polyquaternium-58, polyquaternium-59, polyquaternium-60, polyquaternium-63, polyquaternium-64, polyquaternium-65, polyquaternium-68, or mixtures thereof.

In one embodiment, the polyquaternium polymer includes polyquaternium-2, polyquaternium-4, polyquaternium-6, polyquaternium-7, polyquaternium-11, polyquaternium-16, polyquaternium-22, polyquaternium-28, polyquaternium-32, polyquaternium-37, polyquaternium-39, polyquaternium-42, polyquaternium-47, polyquaternium-51, polyquaternium-53, polyquaternium-55, polyquaternium-58, or mixtures thereof.

In certain embodiments, the cationic oligomer or polymer is characterized by a charge density that may be determined by methods known in the art, such as colloidal titration. In one embodiment, the charge density of the cationic oligomer or polymer is at least about 0.1 meq/g, in another embodiment at least about 2.5 meq/g, and in yet another embodiment, at least about 5 meq/g.

Advantageously, it has been found that disinfecting compositions comprising alcohol and an efficacy-enhancing amount of cationic oligomer or polymer have increased efficacy against a broad spectrum of resident and transient flora, when compared to disinfecting compositions comprising alcohol without cationic oligomer or polymer. Furthermore, disinfecting compositions comprising alcohol, an acid, and an efficacy-enhancing amount of cationic oligomer or polymer have increased efficacy against a broad spectrum of resident and transient flora, when compared to disinfecting compositions comprising alcohol and an acid, without cationic oligomer or polymer.

In one embodiment, an efficacy-enhancing amount of cationic oligomer or polymer is at least about 0.02 percent by weight, based upon the total weight of the disinfecting composition, in another embodiment at least about 0.05, and in yet another embodiment at least about 0.1 percent by weight, based upon the total weight of the disinfecting composition. Generally, an efficacy-enhancing amount of cationic oligomer or polymer is from about 0.02 to about 30 percent by weight, based upon the total weight of the disinfecting composition. In one embodiment, the cationic oligomer or polymer is present in an amount of from about 0.05 to about 10 weight percent, in another embodiment, the cationic oligomer or polymer is present in an amount of from about 0.1 to about 5 percent by weight, in yet another embodiment, from about 0.15 to about 1 percent by weight, and in still yet another embodiment, from about 0.2 to about 0.5 percent by weight, based upon the total weight of the antiviral composition. It will be understood that greater amounts of cationic oligomer or polymer can be employed, if desired, and are expected to perform at least equally as well. As will be understood by one of skill in the art, certain cationic polymers act as thickeners in alcoholic systems, and therefore may affect the viscosity of the disinfecting composition, as well as other aesthetic qualities. In these embodiments, the amount of cationic polymer may be selected within the above ranges to achieve the desired aesthetics. Advantageously, the efficacy of the disinfecting composition is not dependent upon the viscosity of the composition.

In certain embodiments, the cationic oligomer or polymer is added to the disinfecting composition as a solid. In one embodiment, the cationic oligomer or polymer is in a powder form that is dispersible in alcoholic solution. In other embodiments, the cationic oligomer or polymer is added to the disinfecting composition as a solution or emulsion. In other words, the cationic oligomer or polymer may be premixed with a carrier to form a cationic oligomer or polymer solution or emulsion, with the proviso that the carrier does not deleteriously affect the disinfecting properties of the composition. Examples of carriers include water, alcohol, any of the blends described above as carriers for the organic acid, and mixtures thereof. It will be understood that, when the cationic oligomer or polymer is premixed to form a cationic oligomer or polymer solution or emulsion, the amount of solution or emulsion that is added to the disinfecting composition is selected so that the amount of cationic oligomer or polymer falls within the ranges set forth hereinabove.

As described hereinabove, the disinfecting composition of this invention includes an alcohol, an acid, and a cationic oligomer or polymer. The composition can further comprise a wide range of optional ingredients, with the proviso that they do not deleteriously affect the disinfecting efficacy of the composition. By deleterious is meant that the decrease in the log kill according to the FDA TFM surgical hand scrub test is not de minimus, or in other words, the log kill does not decrease by more than about 0.5. The CTFA International Cosmetic Ingredient Dictionary and Handbook, Eleventh Edition 2005, and the 2004 CTFA International Buyer's Guide, both of which are incorporated by reference herein in their entirety, describe a wide variety of non-limiting cosmetic and pharmaceutical ingredients commonly used in the skin care industry, that are suitable for use in the compositions of the present invention. Nonlimiting examples of functional classes of ingredients are described at page 537 of this reference. Examples of these functional classes include: abrasives, anti-acne agents, anticaking agents, antioxidants, binders, biological additives, bulking agents, chelating agents, chemical additives; colorants, cosmetic astringents, cosmetic biocides, denaturants, drug astringents, emulsifiers, external analgesics, film formers, fragrance components, humectants, opacifying agents, plasticizers, preservatives (sometimes referred to as antimicrobials), propellants, reducing agents, skin bleaching agents, skin-conditioning agents (emollient, miscellaneous, and occlusive), skin protectants, solvents, surfactants, foam boosters, hydrotropes, solubilizing agents, suspending agents (nonsurfactant), sunscreen agents, ultraviolet light absorbers, detackifiers, and viscosity increasing agents (aqueous and nonaqueous). Examples of other functional classes of materials useful herein that are well known to one of ordinary skill in the art include solubilizing agents, sequestrants, keratolytics, topical active ingredients, and the like.

Foaming surfactants and/or foam stabilizers may be included, with the proviso that they will not deleteriously affect the antiviral efficacy of the composition. Stable alcoholic foams are further described in co-pending U.S. patent application Ser. No. 11/438,664, which is hereby incorporated by reference in its entirety.

In certain embodiments, the disinfecting composition comprises one or more humectants. Examples of humectants include propylene glycol, dipropyleneglycol, hexylene glycol, 1,4-dihydroxyhexane, 1,2,6-hexanetriol, sorbitol, butylene glycol, propanediols, such as methyl propane diol, dipropylene glycol, triethylene glycol, glycerin (glycerol), polyethylene glycols, ethoxydiglycol, polyethylene sorbitol, and combinations thereof. Other humectants include glycolic acid, glycolate salts, lactate salts, lactic acid, sodium pyrrolidone carboxylic acid, hyaluronic acid, chitin, and the like. In one embodiment, the humectant is present in an amount of from about 0.1 to about 20% by weight, based upon the total weight of the disinfecting composition. In another embodiment the humectant is present in an amount of from about 1 to about 8% by weight, in another embodiment from about 2 to about 3% by weight, based upon the total weight of the disinfecting composition.

In these or other embodiments, the disinfecting composition comprises one or more conditioning or moisturizing esters. Examples of esters include cetyl myristate, cetyl myristoleate, and other cetyl esters, diisopropyl sebacate, and isopropyl myristate. In one embodiment, the ester is present in an amount of up to 10% by weight, based upon the total weight of the disinfecting composition. In another embodiment the ester is present in an amount of from about 0.5 to about 5% by weight, in another embodiment from about 1 to about 2% by weight, based upon the total weight of the disinfecting composition.

In one or more embodiments, the disinfecting composition includes one or more emulsifying agents. Examples of emulsifying agents stearyl alcohol, sorbitan oleate trideceth-2, poloxamers, and PEG/PPG-20/6 dimethicone. In one embodiment, the emulsifying agent is present in an amount of up to about 10% by weight, based upon the total weight of the disinfecting composition. In another embodiment the emulsifying agent is present in an amount of from about 0.1 to about 5% by weight, in another embodiment from about 0.5 to about 2% by weight, based upon the total weight of the disinfecting composition.

In one embodiment, the disinfecting composition includes one or more thickeners and optionally one or more stabilizers. Examples of thickeners and stabilizers include hydroxyethyl cellulose hydroxypropyl cellulose, methyl cellulose, carboxymethyl cellulose, and ammonium acryloyldimethyltaurate/VP copolymer. In one embodiment, where the thickener or stabilizer is starch-based, the thickener or stabilizer is present in an amount of up to about 10% by weight, in another embodiment in an amount of from about 0.1 to about 5% by weight, in yet another embodiment from about 0.2 to about 1% by weight, based upon the total weight of the disinfecting composition. In other embodiments, where the thickener or stabilizer is a synthetic polymer, the thickener or stabilizer is present in an amount of up to about 15% by weight, in another embodiment in an amount of from about 0.1 to about 10% by weight, in yet another embodiment from about 1 to about 2% by weight, based upon the total weight of the disinfecting composition.

In one or more embodiments, the disinfecting composition includes one or more solubilizers. Examples of solubilizers include PEG-40 hydrogenated castor oil, polysorbate-80, PEG-80 sorbitan laurate, ceteareth-20, oleth-20, PEG-4, and propylene glycol. The amount of solubilizer is not particularly limited, so long as it does not deleteriously affect the disinfecting efficacy of the composition.

It has been discovered that the combination of alcohol, acid, and cationic oligomer or polymer exhibits antimicrobial efficacy. In certain embodiments, the disinfecting composition does not contain any auxiliary antimicrobial ingredients. Any antimicrobial ingredient other than the combination of alcohol, acid, and a cationic oligomer or polymer may be referred to as an auxiliary antimicrobial agent. In one embodiment, the amount of auxiliary antimicrobial agent (including preservatives) is less than about 0.1 percent by weight, in another embodiment, less than about 0.05 percent by weight, based upon the total weight of the disinfecting composition. In another embodiment, the disinfecting composition is devoid of auxiliary antimicrobial agents.

It is envisioned that, in other embodiments, auxiliary antimicrobial agents could be included, with the proviso that the antimicrobial ingredient does not deleteriously affect the disinfecting properties of the composition. Examples of auxiliary antimicrobial agents include, but are not limited to, triclosan, also known as 5-chloro-2(2,4-dichlorophenoxy) phenol (PCMX) and available from Ciba-Geigy Corporation under the tradename IRGASAN®; chloroxylenol, also known as 4-chloro-3,5-xylenol, available from Nipa Laboratories, Inc. under the tradenames NIPACIDE® MX or PX; hexetidine, also known as 5-amino-1,3-bis(2-ethylhexyl)-5-methyl-hexahydropyrimidine; chlorhexidine salts including chlorhexidine gluconate and the salts of N,N"-Bis(4-chlorophenyl)-3,12-diimino-2,4,11,14-tetraazatetradecanediimidiamide; 2-bromo-2-nitropropane-1; 3-diol, benzalkonium chloride; cetylpyridinium chloride; alkylbenzyldimethylammonium chlorides; iodine; phenol, bisphenol, diphenyl ether, phenol derivatives, povidone-iodine including polyvinylpyrrolidinone-iodine; parabens; hydantoins and derivatives thereof, including 2,4-imidazolidinedione and derivatives of 2,4-imidazolidinedione as well as dimethylol-5,5-dimethylhydantoin (also known as DMDM hydantoin or glydant); phenoxyethanol; cis isomer of 1-(3-chloroallyl)-3,5,6-triaza-1-azoniaadamantane chloride, also known as quaternium-15 and available from Dow Chemical Company under the tradename DOWCIL™ 2000; diazolidinyl urea; benzethonium chloride; methylbenzethonium chloride; glyceryl laurate, transition metal compounds such as silver, copper, magnesium, zinc compounds, hydrogen peroxide, chlorine dioxide, anilides, bisguanidines, and mixtures thereof. When used, the auxiliary antimicrobial agents are present in amounts of from about 0.1 to about 1 percent by weight, based upon the total weight of the disinfecting composition.

Advantageously, certain ingredients that have been designated as critical to current surgical scrubs and antiseptic compositions can be limited in the disinfecting composition of the present invention. For example, zinc compounds such as organic salts of zinc, zinc gluconate, zinc pyrithione, or zinc omadine are not necessary, and can be limited, if desired, to less than about 0.5 percent by weight, or in another embodiment to less than about 0.1 percent by weight, based upon the total weight of the disinfecting composition. In another embodiment, the disinfecting composition is devoid of organic salts of zinc.

In these or other embodiments, the amount of inorganic salts, aluminum compounds, zirconium compounds, or aluminum-zirconium complexes may be limited. In one or more embodiments, the amount of inorganic salts, aluminum compounds, zirconium compounds, or aluminum-zirconium complexes is less than about 0.05 percent by weight, based upon the total weight of the disinfecting composition.

In certain embodiments, the amount of fatty acid may be limited. In these embodiments, the amount of fatty acid may be less than about 1 percent by weight, in another embodiment less that about 0.1 percent by weight, in yet another embodiment, less than about 0.05 percent by weight, and in still yet another embodiment, less than about 0.01 percent by weight, based upon the total weight of the disinfecting composition. In another embodiment, the disinfecting composition is devoid of fatty acid. In these or other embodiments, the amount of fatty ester may be limited. In these embodiments, the amount of fatty ester may be less than about 1 percent by weight, in another embodiment less that about 0.1 percent by weight, in yet another embodiment, less than about 0.05 percent by weight, and in still yet another embodiment, less than about 0.01 percent by weight, based upon the total weight of the disinfecting composition. In another embodiment, the disinfecting composition is devoid of fatty ester. In these or yet other embodiments, the amount of fatty ether may be limited. In these embodiments, the amount of fatty ether may be less than about 1 percent by weight, in another embodiment less that about 0.1 percent by weight, in yet another embodiment, less than about 0.05 percent by weight, and in still yet another embodiment, less than about 0.01 percent by weight, based upon the total weight of the disinfecting composition. In another embodiment, the disinfecting composition is devoid of fatty ether.

In general, the fatty acids, fatty esters, and fatty ethers that may optionally be limited include those that are claimed in the literature to have antimicrobial properties. Examples of these antimicrobial fatty compounds include (C6-C14) alkyl carboxylic acids, (C6-C14) alkyl carboxylate ester carboxylic acids, (C8-C22) mono- or polyunsaturated carboxylic acids, (C7-C12)saturated fatty acid esters of polyhydric alcohols, (C8-C22)unsaturated fatty acid esters of polyhydric alcohols, (C7-C22)saturated fatty ethers of polyhydric alcohols, (C8-C22)unsaturated fatty ethers of polyhydric alcohols, and alkoxylated derivatives thereof.

Indeed, any component other than the alcohol, acid, and cationic polymer is not necessary to achieve antimicrobial efficacy and can optionally be limited to less than about 0.5 percent by weight, if desired to less than about 0.1 percent by weight, if desired to less than about 0.01 percent by weight, or if desired to less than about 0.001 percent by weight. It will be understood that the balance of the alcoholic composition may, in certain embodiments, include water or other suitable solvent. In one embodiment, the disinfection composition is devoid of any component other than alcohol, acid, cationic polymer, and optionally water or other suitable solvent.

The disinfecting composition may be prepared by simply mixing the components together. In one embodiment, where the cationic oligomer or polymer is obtained as a solid powder, the disinfecting composition is prepared by a method comprising dispersing the cationic oligomer or polymer in water to form a gel, adding alcohol with slow to moderate agitation, and then adding an acid, and optionally other ingredients as desired, and mixing until the mixture is homogeneous.

The physical form of the disinfecting composition is not particularly limited, and in one or more embodiments, the composition may be presented as a liquid that is poured, pumped, sprayed, or otherwise dispensed, a gel, an aerosol, or a foam, including both aerosol and non-aerosol foams. In another embodiment, the disinfecting composition may be presented as a tissue or cloth that is wiped over a surface. The disinfecting composition may be formulated as a rinse-off or rinse-free product.

As stated hereinabove, the disinfecting composition of the present invention may be embodied in a variety of forms, including as a liquid, gel, or foam. Surprisingly, it has been found that the viscosity of the liquid disinfecting composition does not affect the disinfecting efficacy of the composition. For example, in one or more embodiments of the present invention, the same amount of log kill is achieved with a liquid disinfecting composition having a viscosity of 5 centipoise (cPs) and a disinfecting composition having a viscosity of about 2000 cPs. Thus it will be understood that the viscosity of the disinfecting composition of the present invention is not limited.

It will also be understood that the viscosity of the disinfecting composition may be affected by the relative amounts of ingredients. For example, a decrease in the relative amount of certain polyquaternium polymers may result in a lower viscosity. Also, the type of polyquaternium polymer can affect the viscosity of the disinfecting composition.

In one embodiment, the viscosity of the composition is from about 0 cPs to about 5000 cPs, in another embodiment, from about 50 to about 500 cPs, and in another embodiment, from about 100 to about 400 cPs, as measured by Brookfield RV Viscometer using RV and/or LV Spindles at 22° C.+/−3° C.

In one embodiment, where the disinfecting composition is in liquid form, the percent solids of the disinfecting composition is less than about 6 percent, in another embodiment, less than about 5 percent, in yet another embodiment, less than about 4 percent, in still another embodiment, less than about 3 percent, in another embodiment, less than about 2 percent, in yet another embodiment, less than about 1 percent. The percent solids can be determined by various methods known in the art.

In one or more embodiments, the pH of the disinfecting composition is from about 1.5 to about 4.5, in another embodiment from about 2.5 to about 4.2, in another embodiment from about 3 to about 4.

In one or more embodiments, the disinfecting composition of the present invention is applied topically to mammalian skin. In these embodiments, the composition is not applied to the eyes, ears, nose, mouth, or any membranes thereof. In certain embodiments, the present invention provides a method for skin disinfection, the method comprising contacting mammalian skin with an effective amount of a disinfecting composition comprising at least 50 percent by weight alcohol, based upon the total weight of the disinfecting composition, an acid, and a cationic oligomer or polymer.

In one or more embodiments, the method provides a log kill against skin flora of at least about 1 in less than about 1 minute. In other embodiments, the method provides a log kill against skin flora of at least about 2 in less than about 1 minute. In yet other embodiments, the method provides a log kill against skin flora of at least about 3 in less than about 1 minute. The skin flora may include resident and/or transient microbial skin flora. Examples of microbial skin flora include gram positive and gram negative bacteria, and yeast.

Advantageously, the disinfecting composition of the present invention may be used as a pre-surgical scrub or patient pre-operative skin disinfectant. Thus, the present invention provides a method for pre-operative skin disinfection, the method comprising contacting the skin with an effective amount of a disinfecting composition comprising alcohol, an acid, and a cationic oligomer or polymer. The invention further provides a method for pre-surgical hand disinfection, the method comprising contacting the skin with an effective amount of a disinfecting composition comprising alcohol, an acid, and a cationic oligomer or polymer.

Any amount of the disinfecting composition may be used for each application, so long as it is at least an effective amount to contact substantially the entire skin surface. In one embodiment, an effective amount is at least about 1.5 milliliters (mL), in another embodiment at least about 2 mL, in yet another embodiment, at least about 2.5 mL. It will be understood that it is advantageous to achieve adequate efficacy while using a small amount of product. This is true for economic reasons, as well as because the amount of time required for the product to be rubbed into the skin and or evaporated/dried is reduced when less product is used.

In one embodiment, where the disinfecting composition is employed as a pre-surgical hand scrub, the finger nails are maintained with a 1 millimeter free edge and the area under the nails (subungal) are cleaned with a nail pick prior to the first use of the day. Approximately 2 mL of the composition is placed into the palm of one hand. The fingertips of opposite hand are dipped into the product, working it under the nails. The remaining product is spread evenly over the hands and lower ⅔ of one forearm, paying particular attention to the nails, cuticles, and interdigital spaces. Approximately 2 mL of the composition is placed into the palm of the opposite hand and the above procedure is repeated. Finally approximately 2 mL of disinfecting composition may optionally be placed into the palm of either hand and spread evenly over both hands up to the wrists, paying particular attention to nails, cuticles and interdigital spaces and allowed to air dry completely.

The disinfecting composition and method of the present invention provides rapid antimicrobial efficacy upon a single use, without requiring auxiliary antimicrobial agents. As stated hereinabove, requirements for in vitro and in vivo testing of surgical hand scrubs are outlined in the FDA Tentative Final Monograph for Healthcare Antiseptic Drug Products (TFM) (1994). According to the FDA TFM surgical hand scrub test, the test product is used a total of eleven times over a period of five days and the reduction of resident skin flora is measured after the first wash on days 1, 2, and 5 as well as persistent activity 3 and 6 hours after these washes. The protocol is essentially as described below. The first phase of the study is the baseline period. Volunteers refrain from using antimicrobials for two weeks prior to the study. Volunteers clean under fingernails with a nail stick and clip their fingernails. All jewelry is removed from hands and arms. Hands and two thirds of forearms are rinsed with tap water (38° C.-42° C.) for 30 seconds, and then they are washed with a non-antimicrobial soap for 30 seconds and are rinsed for 30 seconds under tap water. Baseline microbial hand counts can then be determined by the glove-juice method described below. This baseline determination is repeated two times on non-consecutive days and subjects exhibiting counts greater than or equal to $1.5 \times 10^5$ after the first and second determination are admitted to the product testing phase of the study.

On day 1 of the test period, a surgical scrub is performed with the test formulation using directions provided by the manufacturer. Subjects perform 3 scrubs on each of days 2, 3, and 4, and a single scrub on day 5.

Hands are sampled at 1 minute, 3 hours, and 6 hours after the first scrubs on day 1, day 2, and day 5. After washing, volunteers wear rubber gloves; 75 mL of sampling solution are then added to one glove, and all surfaces of the hands are massaged for 1 minute. Samples are then taken aseptically and cultured quantitatively. The other glove remains on the other hand for 3 or 6 hours and is sampled in the same manner. The FDA TFM surgical hand scrub test requires that formulations reduce the number of bacteria 1 $\log_{10}$ on the hands within 1 minute of product application and that the bacterial cell count on the hands does not subsequently exceed baseline within 6 hours on day 1; the formulation must produce a 2 $\log_{10}$ reduction in microbial flora on the hands within 1 minute of product application by the end of the second day of enumeration and a 3 $\log_{10}$ reduction of microbial flora on the hands within 1 minute of product use by the end of the fifth day when compared with the established baseline.

In one or more embodiments, the disinfecting composition of the present invention meets or exceeds the requirement of 3 log reduction on day 5. In certain embodiments, the disinfecting composition surpasses the requirements of the FDA TFM surgical hand scrub test by providing greater than about 3 log kill on day 1 of the test, and does not require buildup of antimicrobial activity over repeated use in order to meet the FDA TFM surgical hand scrub test log kill requirements. Less contact time is required to kill transient and resident skin flora. Less volume of the disinfecting composition is needed, and less rub-in time is required.

Advantageously, in one or more embodiments, the disinfecting composition of the present invention also has broad spectrum virucidal efficacy against both enveloped and non-enveloped viruses. The virucidal efficacy is further described in co-pending U.S. application Ser. No. 11/499,227, which is hereby incorporated by reference in its entirety.

In one or more embodiments, the disinfecting composition of the present invention may be employed as a pre-injection skin disinfectant. Thus, a method for pre-injection skin disinfection is provided, the method comprising contacting the skin with an effective amount of a disinfecting composition comprising at least about 50 percent by weight of a $C_{1-6}$ alcohol, based upon the total weight of the disinfecting composition, an acid, and a cationic oligomer or polymer.

In order to demonstrate the practice of the present invention, the following examples have been prepared and tested. The examples should not, however, be viewed as limiting the scope of the invention. The claims will serve to define the invention.

EXAMPLES

Examples 1-9 were prepared according to the formulations shown in Table 2. Examples 8-9 do not contain a cationic polymer, but contain one or more preservatives or auxiliary antimicrobial agents.

TABLE 2

|  | Example # | | | | | | | | |
|---|---|---|---|---|---|---|---|---|---|
|  | 1 | 2 | 3 | 4 | 5 | 6 | 7 | 8 | 9 |
| Ethanol (95%) | 82.11 | 82.11 | 82.11 | 77.89 | 73.68 | 73.68 | 73.68 | 73.68 | 73.68 |
| Polyquaternium-37 | 0.2–0.4 | 0.2–0.4 | 0.2–0.4 | 0.2–0.4 | 0.2–0.4 | 0.2–0.4 | 0.2–0.4 | | |
| Citric Acid | 0.2–0.3 | ≤0.1 | 0.2–0.3 | 0.2–0.3 | 0.2–0.3 | 0.2–0.3 | 0.2–0.3 | 0.4–0.5 | ≤0.1 |
| Humectant | X | X | X | X | | X | X | | X |
| Thickener | | | | | | | | X | X |
| Aminomethyl propanol | | | | | | | | X | |
| Emulsifier Blend | | | | | | | | X | |
| Dimethicone copolyol | | | | | | | | X | |
| Cyclomethicone | | | | | | | | X | |
| Preservative Mix | | | | | | | | X | X |
| Iodopropynyl Butylcarbamate + PEG-4 | | | | | | | | X | |
| PCMX | | | | | | | | | X |
| Benzethonium chloride | | | | | | | | | X |

"X" indicates that this component is present

Example 10 was commercially available product sold under the tradename Avagard. The active ingredients are 61 percent by weight ethanol, and 1 percent by weight chlorhexidine gluconate. Inactive ingredients are beheneth-10, behenyl alcohol, C20-40 pareth-24, cetyl palmitate, diisopropyl dimmer dilinoleate, dimethicone, glycerin, polyethylene glycol, hydroxyethyl urea, squalene, and water.

In Vivo Antimicrobial Efficacy

The Examples were tested under the FDA TFM surgical hand scrub test The study evaluates the antimicrobial efficacy of one (1) test product and three (3) reference products for use as surgical scrubs, with the objective of determining whether the test products would satisfy the critical indices of the FDA TFM surgical hand scrub test, such as: an immediate one (1) $\log_{10}$ reduction in microorganisms on Day 1; an immediate three (3) $\log_{10}$ reduction in microorganisms on Day 5; and that microbial counts from the samples taken approximately six (6) hours to six (6) hours and thirty (30) minutes post-scrub not exceed the baseline counts. The protocol followed is described hereinabove.

The comparative antimicrobial efficacy test data for Examples 1-10 is presented in Table 3. Unless otherwise indicated, the samples were tested by using about 2 mL of sample.

TABLE 3

|  | Day 1 Immediate | Day 1 6 hours | Day 5 Immediate | Day 5 6 hours |
|---|---|---|---|---|
| Example 1 | 3.15 | 3.01 | 3.12 | 3.18 |
| Example 2 | 2.92 | 2.80 | 3.06 | 2.92 |
| Example 3 | 3.39 | 2.61 | 3.68 | 3.36 |
| Example 4 | 3.21 | 2.34 | 3.16 | 2.94 |
| Example 5 | 3.09 | 2.64 | 3.54 | 3.19 |
| Example 6 | 3.31 | 2.22 | 3.66 | 3.38 |
| Example 6[1] | 2.93 | 2.00 | 3.31 | 2.77 |
| Example 7 | 3.24 | 2.13 | 3.50 | 2.94 |
| Example 8 | 3.00 | 2.48 | 3.12 | 2.77 |
| Example 9 | 2.66 | 1.70 | 2.53 | 2.32 |
| Example 10 | 2.30 | 2.60 | 2.96 | 3.17 |

[1]Tested by using 1 mL of product

The data is reported as the immediate log reduction in microbial counts per hand when sampled one minute following the daily scrub over a five day period, and 6 hours later. Log reduction relates to a 10-fold or one decimal or 90% reduction in numbers of recoverable bacteria in a test food vehicle, that is a 1 log reduction would reduce the number of bacteria 90%. This means, for example, that 100 bacteria would be reduced to 10 or 10 reduced to 1. Table 4 represents the percent reduction of bacteria for logs one through five.

TABLE 4

| Microbial Log Reduction Chart | |
|---|---|
| Log Reduction | % Reduction of Bacteria |
| 1 | 90 |
| 2 | 99 |
| 3 | 99.9 |
| 4 | 99.99 |
| 5 | 99.999 |

Thus, it should be evident that the invention herein is advantageous for several reasons including that additional antimicrobial compounds such as preservatives are not needed in the formulations to pass the required surgical scrub test. This is advantageous because addition antimicrobial agents can be irritating or even sensitizing to the skin, they add undue cost and manufacturing time to the formulations, and many have regulatory limitations preventing commercial sale worldwide. In certain embodiments, the method of the present invention provides a 3 log reduction or greater on day 1 instead of requiring several days to achieve a 3 log reduction, as do some current compositions. In one or more embodiments, the disinfecting composition of the present invention provides a 3 log kill or greater each time the product is used as directed. Advantageously, the rapid efficacy of the composition of the present invention provides greater log kill when less product is used. When less product is used, a shorter amount of time is required for the product to be applied to the skin and dried. Thus, the time required for pre-surgical preparation is reduced.

Independent laboratory testing compared irritation potential of commercial products, controls, and a disinfecting composition according to the present invention. The results are shown in Table 5.

TABLE 5

| PRODUCT | CIT Score[3] | Berger & Bowman Classification |
|---|---|---|
| Example 6 | 48.5 | Mild Material |
| SodiumLaurylSulfate[1] | 1321.0 | Possibly Mild in use |
| Johnson andJohnson Baby Oil[2]* | 29.5 | Mild Material |

| Category | Description | CIT Range |
|---|---|---|
| | Mild Material | 0–155 |
| | Probably Mild in Use | 156–620 |
| | Possibly Mild in Use | 621–1399 |
| | Experimental Cumulative Irritant | 1400–1807 |
| | Experimental Primary Irritant | 1808–1953 |

[1]Sodium Lauryl Sulfate is noted as the positive control and known in the industry to be irritating.
[2]Johnson and Johnson Baby Oil is noted as the negative control, and known in the industry to be mild to the skin.
[3]Total Cumulative Irritation.

Certain embodiments of this invention provide a more aesthetically pleasing composition with which to cleanse the hands and forearms prior to surgery and also make donning gloves easier since the product does not leave a sticky residue on the hands. For example, panel testing of a commercially available composition within the scope of U.S. Pat. No. 6,090,395 showed that this product is very thick and has a greasy or slimy feel. It takes a long time to rub in and is sticky after using which makes it difficult to don surgical gloves and also leaves an unpleasant, thick residue on the hands. Sensory panel testing shows that it is less preferred when compared to the compositions of the present invention. Methodology for the panel testing was as follows.

A disinfecting composition according to the present invention (Example 7), and the commercially available scrub composition (CHG-based) were distributed to each panel members in random order, to eliminate any order effect. Participants were instructed to scrub-in with the first product as they normally would before entering a surgery suite. After the product had dried to the participants' liking, they were instructed to don a pair of gloves and complete a questionnaire. Participants washed and dried hands after completion of the questionnaire. The process was repeated with the second product.

The panel participants consisted of 32 operating room healthcare workers from acute care hospitals, aged 25 to 50 years old, free of any skin disorders on their hands, familiar with the surgical scrub process, and who work primarily in operating rooms. Results of the panel testing can be seen in Table 6.

TABLE 6

| QUESTION | CHG-BASED | EX. 7 | P-VALUE | SCALE |
|---|---|---|---|---|
| While using the product, my hands feel slippery | A = 8<br>B = 23<br>(74%) | A = 25<br>(78%)<br>B = 7 | 0.000 | A = Yes<br>B = No |
| While using the product my hands feel sticky | 4.37 | 6.06 | 0.011 | 9 = Strongly Disagree |
| The product leaves my hands feeling sticky | 4.06 | 6.16 | 0.004 | 9 = Strongly Disagree |
| The product leaves an undesirable residue on my hands | 4.06 | 5.21 | 0.112 | 9 = Strongly Disagree |
| My skin feels moisturized after using the product | 4.84 | 5.94 | 0.067 | 9 = Strongly Agree |
| The product leaves my skin feeling clean | 6.09 | 6.94 | 0.099 | 9 = Strongly Agree |
| The product does not affect my ability to don gloves | 6.00 | 6.97 | 0.117 | 9 = Strongly Agree |
| Gloving after use of product is easy | 6.44 | 7.72 | 0.006 | 9 = Strongly Agree |

Overall, composition of the present invention scored higher than the commercially available scrub. The composition of the present invention was significantly better than the commercially available scrub regarding sticky feel and ease of gloving.

In one or more embodiments, the disinfecting composition of this invention provides good product stability over a long-term shelf life. In certain embodiments, the stability of the disinfecting compositions of the present invention is better than the stability of products that are emulsions or solid suspensions. Product stability includes physical properties such as stable viscosity and pH readings over time. Also, product stability requires that the products retain a uniform consistency and appearance, and color and odor must not significantly change so that aged product is different from freshly manufactured product. In one or more embodiments, the disinfecting compositions of the present invention exhibit good product stability over a shelf-life of about three years.

Various modifications and alterations that do not depart from the scope and spirit of this invention will become apparent to those skilled in the art. This invention is not to be duly limited to the illustrative embodiments set forth herein.

What is claimed is:

1. A method for pre-surgical hand disinfection, the method comprising:
    contacting the skin with an effective amount of a disinfecting composition comprising at least about 50 percent by weight of a $C_{1-6}$ alcohol, based upon the total weight of the disinfecting composition; an acid; and a cationic oligomer or polymer, wherein the composition includes less than 0.5 percent by weight of auxiliary antimicrobial agents, and wherein the composition provides a log kill of at least about 3 against resident and transient skin flora in less than about 3 minutes, according to the FDA TFM surgical hand scrub test.

2. The method of claim 1, wherein said composition provides a log kill of greater than about 3 in less than about 2 minutes against resident and transient skin flora, according to the FDA TFM surgical hand scrub test.

3. A method for pre-surgical hand disinfection, the method comprising:
   contacting the skin with an effective amount of a disinfecting composition comprising at least about 50 percent by weight of a $C_{1-6}$ alcohol, based upon the total weight of the disinfecting composition; an acid; and a cationic oligomer or polymer, wherein the composition includes less than 0.5 percent by weight of auxiliary antimicrobial agents, and wherein said composition provides a log kill of greater than about 3 in less than about 1 minutes against resident and transient skin flora, according to the FDA TFM surgical hand scrub test.

4. The method of claim 1, wherein said composition provides a log kill of greater than about 3 against resident and transient skin flora, on the fifth day of use according to the FDA TFM surgical hand scrub test.

5. The method of claim 1, wherein said composition comprises less than 0.5 percent by weight of any zinc compound, and wherein said composition is classified as a Mild Material according to the Berger & Bowman Classification.

6. The method of claim 1, wherein said composition comprises at least about 70 percent by weight of ethanol, based upon the total weight of the disinfecting composition; from about 0.012 to about 1 percent by weight of citric acid, based upon the total weight of the disinfecting composition, and from about 0.02 to about 30 percent by weight of polyquaternium-37, based upon the total weight of the disinfecting composition.

7. The method of claim 6, wherein said composition comprises less than 0.1 percent by weight of auxiliary antimicrobial agents.

8. A method for pre-surgical hand disinfection, the method comprising:
   contacting the skin with an effective amount of a disinfecting composition comprising at least about 70 percent by weight of a $C_{1-6}$ alcohol, based upon the total weight of the disinfecting composition; from about 0.012 to about 1 percent by weight of citric acid, based upon the total weight of the disinfecting composition, and from about 0.02 to about 30 percent by weight of polyquaternium-37, based upon the total weight of the disinfecting composition, wherein the composition provides a log kill of at least about 3 against resident and transient skin flora in less than about 3 minutes, according to the FDA TFM surgical hand scrub test, and wherein said composition is devoid of auxiliary antimicrobial agents.

* * * * *